(12) United States Patent
Ashworth et al.

(10) Patent No.: US 7,479,476 B2
(45) Date of Patent: Jan. 20, 2009

(54) ANTIMICROBIAL COMPOSITIONS COMPRISING POLYMERIC STABILIZERS

(75) Inventors: David Wilson Ashworth, Ruddington (GB); Darren Hodgkinson, Nottingham (GB); Jürgen Huff, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 92 days.

(21) Appl. No.: 10/581,007

(22) PCT Filed: Dec. 1, 2004

(86) PCT No.: PCT/EP2004/013606

§ 371 (c)(1),
(2), (4) Date: May 26, 2006

(87) PCT Pub. No.: WO2005/053398

PCT Pub. Date: Jun. 16, 2005

(65) Prior Publication Data

US 2007/0111915 A1   May 17, 2007

(30) Foreign Application Priority Data

Dec. 4, 2003   (GB)   ................................ 0328156

(51) Int. Cl.
| C11D 7/18 | (2006.01) |
| C11D 7/34 | (2006.01) |
| C11D 7/28 | (2006.01) |
| C11D 3/37 | (2006.01) |

(52) U.S. Cl. .................. 510/385; 510/382; 510/391; 510/398

(58) Field of Classification Search .................. 510/382, 510/385, 391, 398
See application file for complete search history.

(56) References Cited

U.S. PATENT DOCUMENTS

| 5,731,009 A | 3/1998 | Breitenbach et al. |
| 6,627,385 B2 | 9/2003 | Hiller et al. |

FOREIGN PATENT DOCUMENTS

| DE | 43 01 277 | 7/1994 |
| DE | 199 44 464 | 3/2001 |
| EP | 0 726 357 | 8/1996 |
| EP | 1 136 254 | 9/2001 |
| WO | 91/11105 | * 8/1991 |
| WO | WO-91/11105 | 8/1991 |
| WO | WO-95/26137 | 10/1995 |
| WO | WO-95/28841 | 11/1995 |
| WO | WO-97/31643 | 9/1997 |
| WO | WO-00/01237 | 1/2000 |
| WO | WO-00/18237 | 4/2000 |
| WO | 02/054872 | * 7/2002 |
| WO | WO-02/054872 | 7/2002 |

* cited by examiner

Primary Examiner—Charles I Boyer
(74) Attorney, Agent, or Firm—Connolly Bove Lodge + Hutz LLP

(57) ABSTRACT

Antimicrobial composition comprising iodide and thiocyanate anions, periodic acid, and nitrogen and/or phosphorous containing polymers.

35 Claims, No Drawings

ANTIMICROBIAL COMPOSITIONS COMPRISING POLYMERIC STABILIZERS

RELATED APPLICATIONS

This application is a national stage application (under 35 U.S.C. 371) of PCT/EP2004/013606 filed Dec. 1, 2004, which claims benefit to Great Britain application 0328156.5 filed Dec. 4, 2003.

The invention relates to an antimicrobial composition comprising iodide and thiocyanate anions, periodic acid, and nitrogen and/or phosphorous containing polymers.

Antimicrobial compositions comprising iodide and thiocyanate anions in combination with other components such as peroxidases, peroxide donors, D-glucose or oxidoreductase enzymes are well known in the art, i.e. disclosed in WO 91/11105, WO 95/26137, or WO 00/01237.

As an alternative to compositions containing iodide and thiocyanate anions, antimicrobial compositions are known which are based on periodic acid, which is a known oxidising agent and electron acceptor. For example, DE-A-4301277 describes the use of periodic and/or orthoperiodic acid for the sterilisation of containers for storage and transportation of milk by treating the internal surfaces of the container at room temperature for 2-20 seconds with an aqueous solution of 0.1 to 5 wt % of periodic or orthoperiodic acid.

EP-A-0726357 describes a process for inhibiting the production and accumulation of volatile fatty acids by hydrolytic fermentative bacteria in an anionic pulp and paper processing stream in which the presence of hydrogen is monitored and at least one of a biocide and an electron acceptor is added. The use of sodium (para) periodate is recommended for the case where the presence of an electron acceptor and some inhibition of the microorganisms is required.

WO 02/54872 discloses a liquid antimicrobial composition comprising a mixture of iodide and thiocyanate anions and periodic acid or a salt thereof. Furthermore, optionally the composition comprises a peroxidase, specifically a lactoperoxidase. These compositions can be used as microbicide, for example as disinfectant useful to kill viruses and spores. The function of the lactoperoxidase in the system is to increase the shelf-life and long-term efficacy of the system, if necessary, in a specific application.

However, enzymes are an expensive way to achieve this goal, Furthermore, in some cases the use of enzymes may cause damage to certain components of formulations due to their catalytic activity. For instance, hydrogen peroxide will be destroyed by peroxidases.

The problem to be solved by the invention therefore was to substitute enzymes such as peroxidases and oxidoreductases by less expensive and less damaging alternatives.

Surprisingly, it has been found that synthetic polymers or copolymers comprising nitrogen and/or phosphorous groups are suitable to achieve that goal. Shelf-life and long term efficacy is significantly enhanced when using such polymers as additive as compared to solutions without any polymer as well as to solutions comprising polymers not comprising such groups.

Thus, according to one aspect, the invention provides a liquid antimicrobial composition comprising
(1) a mixture of iodide anions and thiocyanate anions;
(2) periodic acid or salt thereof; and
(3) at least one polymer or copolymer obtained by polymerising
  (a) 1 to 100% by weight of at least one monoethylenically unsaturated monomer comprising nitrogen and/or phosphorous containing groups,
  (b) 0 to 99% by weight of at least one monoethylenically unsaturated comonomer comprising acidic groups (a).
  (c) 0 to 99% by weight of at least one further comonomer, and
  (d) 0 to 5% by weight of crosslinking comonomers.

Further embodiments of the invention include the use of such composition as microbicide (e.g. disinfectant or preservative) and a method of killing or suppressing bacteria, yeasts, fungi, viruses or spores by contacting them with the composition.

Regarding the invention, the following may be stated specifically:

As component (1) the antimicrobial composition according to the invention comprises a mixture of iodide anions and thiocyanate anions. The anions are provided as their respective salts. Suitable cations include alkali metal cations, ammonium ions, phosphonium ions, alkaline earth metal cations. Iodide may also be provided as HI. Preferably, the anions are provided as K- or Na-salts.

In a composition embodying the invention, the weight:weight ratio of iodide:thiocyanate anions is preferably from 0.1:1 to 50:1, more preferably from 0.2:1 to 20:1, and most preferably 1:1 to 3:1 inclusive.

As component (2) the antimicrobial composition comprises periodic acid or a salt thereof.

Periodic acid [CAS RN 10450-60-9], sometimes referred to as orthoperiodic acid, has the formula

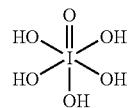

Suitable cations in salts of periodic acid include alkali metal ions, such as $Li^+$, $Na^+$ or $K^+$, alkaline earth metal ions, such as $Mg^{2+}$ or $Co^{2+}$, ammonium and alkylammonium cations, such as $NH_3R^+$, $NH_2R_2^+$, $NHR_3^+$ and $NR_4^+$ where R stands for—independently—an organic residue, preferably a $C_1$-$C_{10}$-alkyl- or aralkyl-residue.

As component (3) the antimicrobial composition comprises a polymer or copolymer as defined above.

Examples of suitable monoethylenically unsaturated monomers (a) with nitrogen containing groups include nitrogen containing acrylic acid derivatives such as acrylamide, N-substituted H-acrylamides or nitrogen containing acrylic acid esters such as dimethylaminoethylmethacrylate, N-vinylamides such as N-vinylformamide, N-vinyl-N-methylformamide, N-vinylacetamide, N-vinyl-N-methylacetamide, N-vinyl-N-methylpropionamide and N-vinylpropionamide. Further suitable monomers are N-vinylimidazole and N-vinyl lactams containing 5 to 13 carbon atoms in the lactam ring. Examples include N-vinylpyrrolidone, N-vinylbutylrolactam, N-vinylcaprolactam, N-vinylvalerolactam and N-vinyllaurolactam.

Monomer units may also be modified after polymerization. If the N-containing groups are hydrolyseable the groups may be hydrolysed.

Examples of suitable monomers with phosphorous containing groups include vinyl phosphonic acid esters.

At least one of these monomers (a) is used as component, i.e. the resulting polymer may be a homopolymer. However, it is preferred that the polymer is a copolymer of at least two different monomers (a) or at least one monomer (a) and at least one further monomer (b) and/or (c).

A preferred combination of two monomers (a) includes vinylimidazole and N-vinyl-pyrrolidone.

The amount of the monomers (a) in the polymer is from 1 to 100% by weight, regarding to the total weight of the polymer. Preferably, the amount is from 5 to 100%, more preferred from 10 to 60%, and most preferred from 15 to 50%.

Comonomers (b) comprise at least one acidic group or a derivative thereof such as salts or anhydrides. Examples of acidic groups include —COOH-groups, phosphorous acid groups, phosphonic acid groups or sulfonic acid groups.

Examples of suitable comonomers (b) include acrylic acid, methacrylic acid, maleic acid, fumaric acid, vinyl sulfonic acid, vinyl phosphonic acid or phosphorous acid monovinylester or phosphorous acid mono allylester.

Preferred monomers (b) are acrylic acid, methacrylic acid and maleic acid. Comonomer (b) may be present in an amount of 0% up to 99%. Preferably, the amount is from 0 to 95%, more preferred from 20 to 70%, and most preferred from 25 to 65%.

Two different types of comonomers (c) may be used. One type includes monoethylenically unsaturated monomers different from (a) and (b), i.e. not comprising nitrogen- or phosphorous containing groups or acidic groups, however copolymerizable with (a) and (b) by the same polymerization technique.

Suitable examples include olefins like ethylene or propylene, vinylaromatic monomers such as styrene, vinylalkohol or its esters such as vinylacetate or vinylpropionate or esters of acrylic acid or methacrylic acid.

A second type of comonomers (c) does not comprise ethylenically unsaturated groups, and such comonomers are not copolymerizable by the same polymerization technique with the monomers (a) and (b). Examples of such comonomers (c) include monomers suitable for the formation of polyethers, especially alkylene oxides such as ethylene oxide, propylene oxide or butylene oxide or 1,ω-Dialcohols such as ethylene glycol, 1,3-propandiol, 1,4 butanediol or cyclic ethers such as THF.

Preferred comonomers (c) include ethylene oxide, propylene oxide, ethylene glycol, 1,3-propandiol and 1,4 butanediol.

Comonomers (c) may be present in an amount of 0 to 99%, preferably 0 to 75%, more preferred 20 to 70%, and most preferred 20 to 60%.

Polymers and copolymers of said monomers may be made by any of the known polymerization technologies known to a person skilled in the art. Preferably, the polymerization is performed by free radical polymerization of the component (a), optionally (b), and optionally first type monomers (c). The polymerization can be performed in solution, dispersion, suspension, emulsion or bulk. Suitable conditions are known to a person skilled in the art.

If the second type (c) monomers are used two different polymerization techniques have to be used. At first a polyether is formed using said monomers (c), for instance, by cationic polymerization or by polycondensation. A preferred polyether is polyethyleneoxide. In a second step the monomers (a) and optionally (b) are polymerized by free radical poly-merisation in the presence of the polyether. Under these conditions, graft polymers are formed. Details of this technology are disclosed for instance in EP-A 1 136 254 and the literature cited therein. Of course, chains of (a) and optionally (b) monomers and chains of (c) monomers can be linked together by other techniques known to the skilled artisan.

As compound (d) the polymer may comprise additionally a crosslinker; however, excessive crosslinking should be avoided. If present at all, the amount of a crosslinker should not exceed 5% by weight, preferably not more than 3%, and most preferred not more than 2%. Examples of suitable crosslinkers comprise monomers with two or more ethylenically unsaturated groups which are not conjugated, such as butandioldi(meth)acrylate or hexanedioldi(meth)acrylate.

The properties of the polymers used according to the present invention can be influenced by the skilled artisan by the choice of the amount and nature of monomers (a) and optionally (b) and/or (c) and/or (d). It is possible to obtain water-soluble polymers or polymers soluble in oil.

For the purpose of this invention it is preferred to use polymers which are soluble or at least dispersible in water.

The antimicrobial composition according to the invention can be used as such or by combining/mixing separate solutions of the components. It may be added, preferably after intense mixing of the components with each other, directly to a medium to be protected.

Preferably however, the compositions should be formulated into pastes, emulsions, solutions or put onto solid carriers.

Preferably, the composition is a liquid composition and also preferably the composition comprises water.

A water comprising composition may be a solution of all components in a suitable solvent mixture. Preferably, a suitable solvent mixture comprises at least 50% by weight of water, more preferred at least 80%, and most preferred the solvent is only water. Additional components of a solvent mixture may be organic solvent miscible with water. Examples of suitable components comprise monoalcohols such as methanol, ethanol, 1-propanol or 2-propanol, dialcohols such as ethylene glycol or 1,4 butandiol and also polyetheralcohols such as diethyleneglycol.

The composition may also comprise additionally a surfactant or emulsifier, whereby the composition is an oil-in-water emulsion or a surfactant based solution.

The composition may also comprise further additives and auxiliaries such as dyes, corrosion inhibitors, salts, fragrances, anti-foaming agents, surfactants, emulsifiers or chelants.

The composition can be used in combination with other actives such as adipic acid, benzoic acid, biphenyl-2-ol, bronopol, calcium hypochlorite, cetylpyridinium chloride, chlorocresol, chloroxylenol, compound of D-gluconic acid with N,N"-bis(4-chloro-phenyl)-3,12-diimino-2,4,11,13 tetraazatetradecanediamidine (2:1), 2,2-Dibromo-2-cyanoacetamide, ethanol, formaldehyde, formic acid, glutaraldehyde, hexa-2,4-dienoic acid, hydrogen peroxide, iodine, 1-phenoxypropan-2-ol and 2-phenoxypropanol, L-(+)-lactic acid, oligo-(2-(2-ethoxy)ethoxyethyl guanidinium chloride), pentapotassium bis(peroxymonosulphate) bis(sulphate), peracetic acid, 2-phenoxyethanol, orthophthalaldehyde, 6-(phthalimido)peroxyhexanoic acid, poly(hexamethylendiamine guanidinium chloride), potassium (E,E)-hexa-2,4-dienoate, propan-1-ol, propan-2-ol, quaternary ammonium compounds, e.g. benzyl-alkyldimethyl ammonium chloride, [2-[[2-[(2-Carboxyethyl)(2-hydroxyethyl)amino]ethyl]amino]-2-oxoethyl]coco alkyldimethyl ammonium hydroxide, benzyl-$C_{12-14}$-alkyldimethyl ammonium chloride, benzyl-$C_{12-16}$-alkyldimethyl ammonium chloride, benzyl-$C_{12-18}$-alkyldimethyl ammonium chloride, $C_{12-14}$-alkyl[(ethylphenyl)methyl]dimethyl ammonium chloride, reaction products of n-$C_{10-16}$-alkyltrimethylenediamines with chloroacetic acid, di-$C_{8-10}$-alkyldimethyl ammonium chloride, dialkyl ($C_{8-18}$)dimethyl ammonium compounds, didecyidimethylammonium chloride, cetylpyridinium chloride, reaction products of glutamic acid and N—($C_{12-14}$-alkyl)propylenediamine, salicylic acid, silver chloride or other silver salts, sodium 2-biphenylate, sodium dichloroisocyanurate dihydrate, sodium dichloro-s-tria-zinetrione, sodium hypochlorite, sodium p-chloro-m-cresolate, sodium tosylchloramide.

Preferred combination products are chlorocresol, chloroxylenol, ethanol, formaldehyde, formic acid, glutaraldehyde, hydrogen peroxide, 1-phenoxypropan-2-ol and 2-phenoxypropanol, 2-phenoxyethanol, ortho-phthalaldehyde, polyhexamethylene biguanide, propan-1-ol, propan-2-ol or quaternary ammonium compounds as mentioned above.

The compositions embodying the invention can be used as microbicides, e.g. as a preservative or as a disinfectant.

In particular, compositions embodying the invention are particularly effective in combating bacteria, yeasts, fungi, viruses and spores, e.g. bacillus spores.

Typical concentrations for application are:

| component | typical concentration | Preferred |
|---|---|---|
| periodic acid or salts thereof | 0.01-100 mmol/l | 0.05-10 mmol/l |
| iodide ions | 0.005-50 mmol/l | 0.05-10 mmol/l |
| thiocyanate ions | 0.005-50 mmol/l | 0.05-10 mmol/l |
| (co)polymer | 0.005-10% by weight | 0.1-5% by weight |

It is of course possible to formulate a composition as a concentrate and to dilute it before use. The components may be formulated as separate concentrates. In the same manner, a concentrate or the component concentrates may be added to the medium to be protected leading to the concentrations mentioned above.

The pH of the composition may be from, 1 to 8 but is preferably less than 6.0 and, especially at low pH, the composition may contain free periodic acid. However, the composition may alternatively or additionally contain an alkali metal, especially the sodium, salt thereof. The pH may be adjusted using a suitable buffer system.

The application areas the compositions can be used in are: skin antiseptics; antimicrobial soaps; suntans; disinfection of medical equipment; treatment of swimming pools etc., air-conditioning processes; sanitation of accomodation for man; chemical toilets; treatment of sewage/waste, hospital infectious waste and soil or other substances; laundry; disinfection of animal housing/stables/machinery/footwear, hatcheries, means of transport; fish farming; floors, walls, and equipment in food processing plants; manufacture of aseptic packaging material.

In addition to the use of the composition as a microbicide (for instance as a preservative or a disinfectant as described above), an anti-microbial composition embodying the invention may provide the active component in a wide variety of products which require potent antiviral, antibacterial, anti-mould and/or anti-yeast activities. Examples of such products include:

a) deodorants e.g. for topical administration in the form of lotions;

b) antibacterial skin washes e.g. in the forms of lotions;

c) anti-acne preparations e.g. in the form of lotions or creams;

d) anti-athletes foot preparations e.g. in the form of lotions;

e) anti-dandruff preparations e.g. in the form of shampoos or lotions;

f) dental preparations, e.g. mouth washes suitable for general oral hygiene and, in particular, having anti-plaque properties, and dentrifices such as toothpastes, chewing gums and lozenges;

g) impregnated materials e.g. wound dressings, sutures and dental floss;

h) pharmaceuticals e.g. wound irrigants and burn treatments, anti-diarrhoeal agents and medicaments suitable for the treatment of infections such as Candida and Tinea infections;

i) opthalmic preparations e.g. eye washes and/or sterilising contact lenses; and j) sterilants e.g. for baby bottles and surgical or dental instruments.

According to yet another aspect, the invention provides a method of killing or suppressing viruses or spores comprising contacting them within a composition as defined above.

The composition embodying the invention can be used by treating objects to be protected, such as for instance medical equipment and the like with the composition. This may be done for example by dipping the objects into a solution or by spraying the objects with a solution.

Furthermore, the composition can be added to the medium to be protected. In the latter case, a solution of all components may be used, but it is of course also possible to add the components separately; i.e. a solution of the salts and one of the polymer. For the scope of the invention is only necessary the all components are present in the medium to be protected.

Embodiments of the invention will now be described in more detail with reference to the following Examples.

EXAMPLES

For all examples and comparative examples a solution of NaSCN, NaI, and periodic acid in water was used (pH 3.8).

The concentration of all samples was: 0.9 mmol/l periodate, 0.4 mmol/l iodide, and 0.6 mmol/l thiocyanate.

To each of these solutions polymers in the concentration as shown in table 1 were added. For comparative purposes 1 sample remained without any polymer.

The examples summarized in table 1 were made up by dissolving all the components in water to give the required concentrations. The solutions were stored at ambient temperature and tested at the storage points described in table 1. The testing procedure comprises of taking a sample of the stored solution and inoculating with the organisms as described in table 1. If after 5 minutes contact time with the solution then a 5 log reduction of the organism can be shown, then the solution has met the test criteria for a positive result.

All experiments are summarized in table 1

TABLE 1

|  | Polymer | concentration [ppm] | 24 hrs storage | 1 month storage | 3 months storage |
|---|---|---|---|---|---|
| Example 1 | Copolymer of acrylic acid (75% w/w) and vinyl pyrrolidone (25% w/w) | 1000 | + | + | + |
|  |  | 500 | + | + | + |
|  |  | 200 | + | + | + |
|  |  | 100 | + | − | − |
| Example 2 | Co-polymer of vinyl imdazole (50% w/w) and vinyl pyrrolidone (50% w/w) | 1000 | + | + | + |
|  |  | 500 | + | + | + |
|  |  | 200 | + | + | + |
|  |  | 100 | + | − | − |
| Example 3 | Co-polymer of Vinyl pyrrolidone (30% w/w), vinyl imidazole (30% w/w) grafted onto polyethylene oxide (40% w/w) | 1000 | + | + | + |
|  |  | 500 | + | + | + |
|  |  | 200 | + | + | + |
|  |  | 100 | + | + | − |
| Comparative | Polyacrylic acid | 1000 | + | − | − |
|  |  | 500 | + | − | − |

TABLE 1-continued

| Polymer | | concentration [ppm] | 24 hrs storage | 1 month storage | 3 months storage |
|---|---|---|---|---|---|
| Example 1 | | 200 | + | – | – |
| | | 100 | + | – | – |
| Comparative Example 2 | Polyethylene oxide | 1000 | + | – | – |
| | | 500 | + | – | – |
| | | 200 | + | – | – |
| | | 100 | + | – | – |
| Comparative Example 3 | No polymer | n/a | + | – | – |

Key
+ Passes. At least 5 log reduction of *Aspergillus niger* and *Escherichia coli* in 5 minutes after one month storage of the mixture
– Fails. Less than 5 log reduction of *Aspergillus niger* and *Escherichia coli* in 5 minutes after one month storage of the mixture The examples and comparative examples clearly demonstrate that the use of polymers comprising N- or P-containing groups significantly increases the stability and long-term activity. Polymers without such groups do not demonstrate such an effect.

The invention claimed is:

1. An antimicrobial composition comprising
   (1) a mixture of iodide anions and thiocyanate anions,
   (2) periodic acid or a salt thereof, and
   (3) at least one copolymer comprising as units
      (a) 5 to 100% by weight of at least one monoethylenically unsaturated monomer comprising nitrogen and/or phosphorous containing groups,
      (b) 0 to 95% by weight of at least one monoethylenically unsaturated comonomer comprising acidic groups,
      (c) 0 to 75% by weight of at least one further comonomer, and
      (d) 0 to 5% by weight of crosslinking comonomers and wherein there are at least two different units of (a).

2. A composition according to claim 1, wherein the amounts of the units of the copolymer are:
   (a) 10 to 60%,
   (b) 20 to 70%,
   (c) 0 to 70%, and
   (d) 0 to 5%.

3. A composition according to claim 1, wherein the composition is a liquid composition.

4. A composition according to claim 3, wherein the liquid composition comprises a solvent and said solvent comprises at least 80% water.

5. A composition according to claim 3, wherein the concentrations of the components in the solution are
   0.01 to 100 mmol/l periodic acid or salts thereof,
   0.005 to 50 mmol/l iodide ions,
   0.005 to 50 mmol/l thiocyanate ions, and
   0.005 to 10% by weight copolymer.

6. A composition according to claim 1, wherein the composition further comprises another biocidal active compound.

7. A composition according to claim 3, wherein the composition further comprises a surfactant or emulsifier and the liquid composition is an oil-in-water-emulsion or a surfactant based solution.

8. A microbicide for skin antiseptics; antimicrobial soaps; suntans; disinfection of medical equipment; treatment of swimming pools, air-conditioning processes; sanitation of accomodation for man; chemical toilets; treatment of sewage/waste, hospital infectious waste and soil or other substances; laundry; disinfection of animal housing/stables/machinery/footwear, hatcheries, means of transport; fish farming; floors, walls, and equipment in food processing plants; or the manufacture of aseptic packaging material which comprises the composition as claimed in claim 1.

9. An active component which comprises the composition as claimed in claim 1.

10. The active component as claimed in claim 9, wherein the active component is used in deodorants, antibacterial skin washes, anti-acne preparations, anti-athletes foot preparations, anti-dandruff preparations, dental preparations, impregnated materials, ophthalmic preparations or sterilants.

11. The composition according to claim 1, wherein the copolymer comprises as monomer
   (a) vinylimidazole and N-vinylpyrrolidone.

12. An antimicrobial composition comprising
   (1) a mixture of iodide anions and thiocyanate anions,
   (2) periodic acid or a salt thereof, and
   (3) at least one copolymer comprising as units
      (a) at least 5% by weight of at least one monoethylenically unsaturated monomer comprising nitrogen and/or phosphorous containing groups,
      (b) 0 to 95% by weight of at least one monoethylenically unsaturated comonomer comprising acidic groups,
      (c) up to 75% by weight of at least one further comonomer that is different from (a) and (b) and is a monoethylenically unsaturated monomers selected from the group consisting of
         ethylene,
         propylene,
         vinylaromatic monomers,
         vinylalkohol or its esters,
         vinylpropionate,
         esters of acrylic acid,
         esters of methacrylic acid,
         alkylene oxide,
         1,ω-dialcohol and
         cyclic ether and
      (d) 0 to 5% by weight of crosslinking comonomers
      wherein component (c) is present.

13. The antimicrobial composition according to claim 12, wherein the comonomer (c) is styrene, vinylacetate, vinylpropionate, ethylene oxide, propylene oxide, ethylene glycol, 1,3-propandiol, 1,4 butanediol or tetrahydrofuran.

14. The composition according to claim 12, wherein the amounts of the units of the copolymer are:
   (a) 10 to 60%,
   (b) 20 to 70%,
   (c) 0 to 70%, and
   (d) 0 to 5%.

15. The composition according to claim 12, wherein the composition is a liquid composition.

16. A composition according to claim 15, wherein the concentrations of the components in the solution are
   0.01 to 100 mmol/l periodic acid or salts thereof
   0.005 to 50 mmol/l iodide ions,
   0.005 to 50 mmol/l thiocyanate ions, and
   0.005 to 10% by weight copolymer.

17. The composition according to claim 12, wherein the composition further comprises another biocidal active compound.

18. The composition according to claim 15, wherein the composition further comprises a surfactant or emulsifier and the liquid composition is an oil-in-water-emulsion or a surfactant based solution.

19. A microbicide for skin antiseptics; antimicrobial soaps; suntans; disinfection of medical equipment; treatment of swimming pools, air-conditioning processes; sanitation of accomodation for man; chemical toilets; treatment of sewage/waste, hospital infectious waste and soil or other substances; laundry; disinfection of animal housing/stables/machinery/footwear, hatcheries, means of transport; fish farming; floors, walls, and equipment in food processing plants; or the manufacture of aseptic packaging material which comprises the composition as claimed in claim 12.

20. An active component which comprises the composition as claimed in claim 12.

21. The active component as claimed in claim 20, wherein the active component is used in deodorants, antibacterial skin washes, anti-acne preparations, anti-athletes foot preparations, anti-dandruff preparations, dental preparations, impregnated materials, ophthalmic preparations or sterilants.

22. An antimicrobial composition comprising
    (1) a mixture of iodide anions and thiocyanate anions,
    (2) periodic acid or a salt thereof, and
    (3) at least one polymer or copolymer comprising as units
        (a) at least 5% by weight of at least one monoethylenically unsaturated monomer comprising nitrogen and/or phosphorous containing groups which are selected from the group consisting of acrylamide, N-substituted H-acrylamide, nitrogen containing acrylic acid ester, N-vinylamide N-vinyl-N-methylformamide, N-vinylacetamide, N-vinyl-N-methylacetamide, N-vinyl-N-methylpropionamide, N-vinylpropionamide, N-vinylimidazole N-vinylbutylrolactam, N-vinylcaprolactam, N-vinylvalerolactam and N-vinyllaurolactam.
        (b) 0 to 95% by weight of at least one monoethylenically unsaturated comonomer comprising acidic groups,
        (c) 0 to 75% by weight of at least one further comonomer, and
        (d) 0 to 5% by weight of crosslinking comonomers.

23. The antimicrobial composition according to claim 22, wherein the comonomer (a) is dimethylaminoethylmethacrylate, N-vinylformamide, N-vinyl-N-methylformamide, N-vinylacetamide, N-vinyl-N-methylacetamide, N-vinyl-N-methylpropionamide, N-vinylpropionamide, N-vinylimidazole N-vinylbutylrolactam, N-vinylcaprolactam, N-vinylvalerolactam or N-vinyllaurolactam.

24. The composition according to claim 22, wherein the amounts of the units of the copolymer are:
    (a) 10 to 60%,
    (b) 20 to 70%,
    (c) 0 to 70%, and
    (d) 0 to 5%.

25. The composition according to claim 22, wherein the composition is a liquid composition.

26. The composition according to claim 25, wherein the concentrations of the components in the solution are 0.01 to 100 mmol/l periodic acid or salts thereof,
0.005 to 50 mmol/l iodide ions,
0.005 to 50 mmol/l thiocyanate ions, and
0.005 to 10% by weight polymer or copolymer.

27. The composition according to claim 22, wherein the composition further comprises another biocidal active compound.

28. The composition according to claim 25, wherein the composition further comprises a surfactant or emulsifier and the liquid composition is an oil-in-water-emulsion or a surfactant based solution.

29. The composition according to claim 22, wherein said copolymer further comprises N-vinylpyrrolidone.

30. A microbicide for skin antiseptics; antimicrobial soaps; suntans; disinfection of medical equipment; treatment of swimming pools, air-conditioning processes; sanitation of accomodation for man; chemical toilets; treatment of sewage/waste, hospital infectious waste and soil or other substances; laundry; disinfection of animal housing/stables/machinery/footwear, hatcheries, means of transport; fish farming; floors, walls, and equipment in food processing plants; or the manufacture of aseptic packaging material which comprises the composition as claimed in claim 22.

31. An active component which comprises the composition as claimed in claim 22.

32. The active component as claimed in claim 31, wherein the active component is used in deodorants, antibacterial skin washes, anti-acne preparations, anti-athletes foot preparations, anti-dandruff preparations, dental preparations, impregnated materials, ophthalmic preparations or sterilants.

33. The composition as claimed in claim 1, wherein unit b is at least one monoethylenically unsaturated comonomer comprising an acidic group selected from the group consisting of acrylic acid, methacrylic acid, maleic acid, fumaric acid, vinyl sulfonic acid, vinyl phosphonic acid or phosphorous acid monovinylester and phosphorous acid mono allylester.

34. The composition as claimed in claim 12, wherein unit b is at least one monoethylenically unsaturated comonomer comprising an acidic group selected from the group consisting of acrylic acid, methacrylic acid, maleic acid, fumaric acid, vinyl sulfonic acid, vinyl phosphonic acid or phosphorous acid monovinylester and phosphorous acid mono allylester.

35. The composition as claimed in claim 22, wherein unit b is at least one monoethylenically unsaturated comonomer comprising an acidic group selected from the group consisting of acrylic acid, methacrylic acid, maleic acid, fumaric acid, vinyl sulfonic acid, vinyl phosphonic acid or phosphorous acid monovinylester and phosphorous acid mono allylester.

* * * * *